United States Patent [19]
Tittmann et al.

[11] 4,274,288
[45] Jun. 23, 1981

[54] METHOD FOR MEASURING THE DEPTH OF SURFACE FLAWS

[75] Inventors: Bernhard R. Tittmann; Lloyd A. Ahlberg, both of Thousand Oaks, Calif.

[73] Assignee: Rockwell International Corporation, El Segundo, Calif.

[21] Appl. No.: 59,822

[22] Filed: Jul. 23, 1979

[51] Int. Cl.³ .............................................. G01N 29/04
[52] U.S. Cl. ....................................................... 73/602
[58] Field of Search ................... 73/602, 799, 597, 645

[56] References Cited
U.S. PATENT DOCUMENTS

| | | | |
|---|---|---|---|
| 3,662,589 | 5/1972 | Adler et al. .............................. | 73/602 |
| 3,996,791 | 12/1976 | Niklas et al. ............................. | 73/602 |
| 4,052,889 | 10/1977 | Mucciardi et al. ....................... | 73/602 |
| 4,098,129 | 7/1978 | Deblaere et al. ........................ | 73/602 |

OTHER PUBLICATIONS

Doyle, P. A. et al., Crack Depth Measurement by Ultrasonics: A Review, from Ultrasonics, Jul. 1978, pp. 164–170.

Primary Examiner—Jerry W. Myracle
Attorney, Agent, or Firm—H. Fredrick Hamann; Craig O. Malin; John J. Deinken

[57] ABSTRACT

Disclosed is a method for measuring the depth a of a surface flaw in an object, including the steps of irradiating the flaw with an incident acoustic surface wave signal, detecting a reflected acoustic surface wave signal, including a first portion reflected from the surface edge of the flaw and a second portion reflected from the bottom of the flaw, and analyzing the interference between the first and second portions of the reflected signal to determine the depth of the flaw. The analysis may be carried out by Fourier transforming the reflected signals from the time domain to the frequency domain, selecting a frequency $f_n$ for which a maximum or minimum amplitude is detected independent of the angle of detection, and calculating the depth a from the formula $a = nV_r/2f_n$, where n is an integer, and $V_r$ is the speed of an acoustic surface wave in the object.

12 Claims, 4 Drawing Figures

METHOD FOR MEASURING THE DEPTH OF SURFACE FLAWS

GOVERNMENT RIGHTS

The invention herein described was made under a contract with the U.S. Air Force.

BACKGROUND OF THE INVENTION

This invention is related to the field of nondestructive testing, and more particularly, to nondestructive testing utilizing ultrasonic waves.

The significant contributions which surface cracks make to the fracture of structural materials have recently become well recognized, with such cracks receiving more concentrated attention toward accurately and effectively predicting the failure of materials. A number of ultrasonic methods have been applied to the measurement of surface cracks in the past. Such prior art methods have utilized both bulk and surface wave methods, including pulse echo techniques, depth measurement from first principles, timing methods, and spectroscopic analysis. The known techniques, however, are subject to a number of shortcomings. Moreover, recent developments involving surface waves have provided new techniques for exciting high frequency waves and for generating such waves with increased efficiencies. Thus, a need has developed in the art for a surface wave flaw depth measurement method which may be related to the context of the fracture mechanics of part through cracks to delineate the stress intensity range and determine the remaining fatigue life for structural materials.

SUMMARY OF THE INVENTION

It is a general object of this invention to provide a new and improved method for measuring the depth of a flaw in a material utilizing acoustic surface waves.

A method for measuring the depth of a surface breaking flaw in an object, according to this invention, includes the steps of:

(a) irradiating the flaw with an incident acoustic surface wave signal, (b) detecting a reflected acoustic surface wave signal, including a first portion reflected from the surface edge of the flaw and a second portion reflected from the bottom of the flaw, and (c) determining the depth of the flaw by analyzing the interference between the first and second portions of the reflected signal.

The incident signal may further be a short pulse signal containing a broadband of frequencies, in which case the reflected signal is detected at at least two different angles with respect to the normal to the flaw direction and the interference analysis is performed by transforming the reflected signals from the time domain to the frequency domain, selecting a frequency $f_n$ for which a maximum amplitude is detected independent of the angle of detection, and calculating the depth a from the formula:

$$a = (n\, V_R/2\, f_n)$$

where:
n is an integer, and
$V_R$ is the speed of an acoustic surface wave in the object.

Alternatively, the depth may be determined from the same formula by taking measurements at one angle, transforming the reflected signal from the time domain to the frequency domain, and computing the depth utilizing a frequency $f_n$ representing the nth minimum in the frequency domain of the reflected signal.

In another embodiment, the flaw is irradiated with a series of incident acoustic surface wave signals, each at a different frequency. The method then includes detecting, for each incident signal, a reflected acoustic surface wave signal at at least two different angles with respect to the normal to the flaw direction. The frequency $f_n$ for which a maximum amplitude is detected independent of the angle of detection is then selected, and the depth a is calculated from the above formula.

Examples of the more important features of the invention have been broadly outlined in this Summary in order to facilitate an understanding of the detailed description that follows and so that the contributions which this invention provides to the art may be better appreciated. There are, of course, additional features of the invention, which will be described below and which are included within the subject matter of the appended claims.

BRIEF DESCRIPTION OF THE DRAWINGS

Additional objects, features, and advantages of the present invention will become apparent by referring to the detailed description below of the preferred embodiments, in connection with the accompanying drawings, wherein like reference numerals refer to like elements throughout all the figures. In the drawings.

DESCRIPTION OF THE PREFERRED EMBODIMENTS

Figure 1:
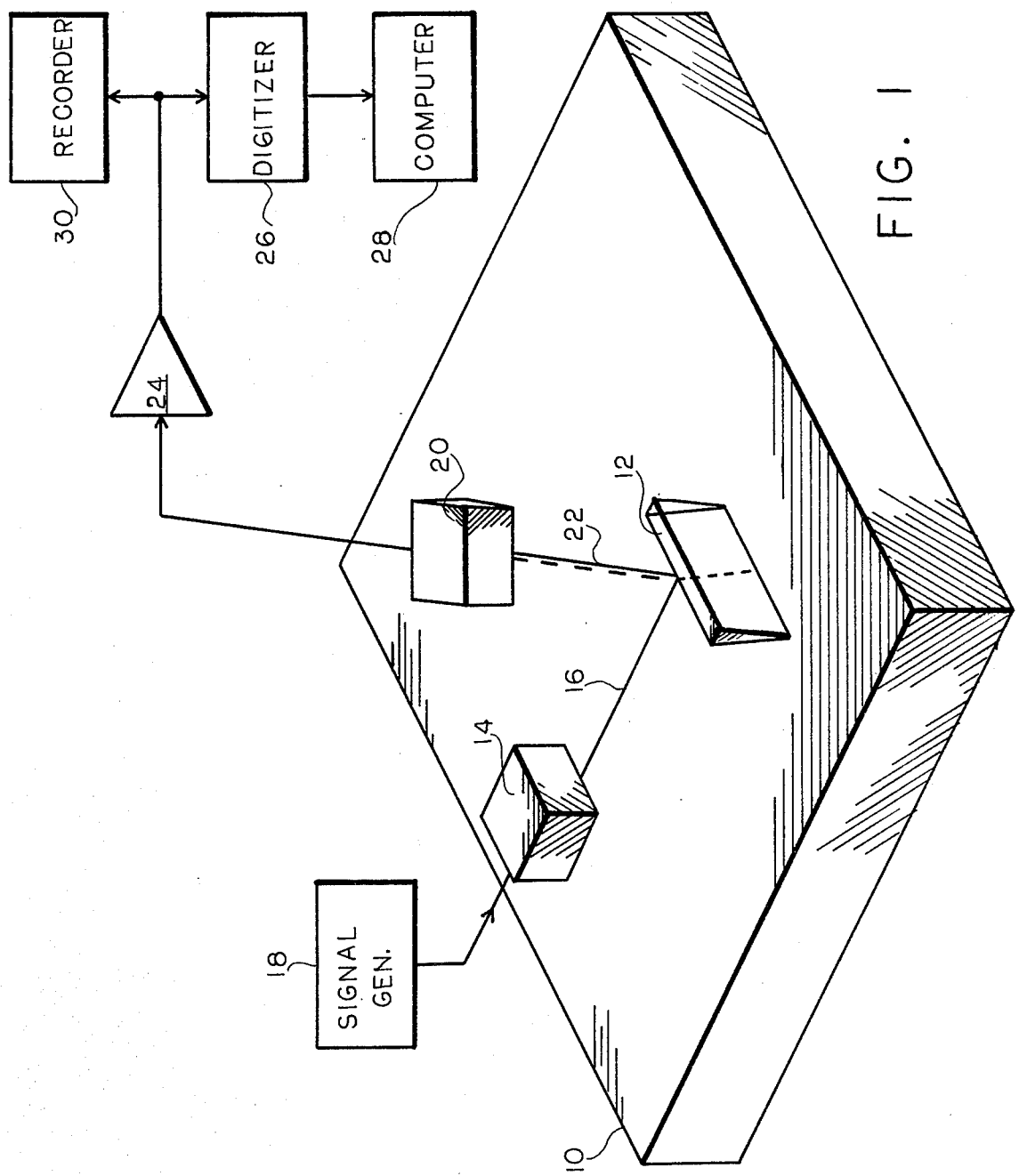
FIG. 1 is a perspective view in partial schematic of an apparatus which may be utilized to practice the method of this invention.

Since failure prediction is the ultimate objective of quantitative nondestructive evaluation, the proper approach to this goal should delineate the important fracture mechanics parameters and inquire what ultrasonics measurements must be made, and how they must be interpreted, to obtain these parameters as directly and accurately as is needed for failure prediction.

Crack growth under cyclic fatigue takes place over a relatively long period of time. Thus, it is important, in developing fracture mechanics parameters, to speak in terms of a stress intensity range and a remaining life in terms of the number of cycles remaining before failure. The stress intensity range $\Delta K_i$ is $$\Delta K_i = C\, \Delta\sigma\, \sqrt{a/Q} \tag{1}$$

where:
C = 1.95, $$Q = \phi^2 - 0.212 \left(\frac{\sigma_{max}}{\sigma_{yield}}\right)^2,$$

$$\phi = \int_0^{\pi/2} [\sin^2\psi + (a/c)^2 \cos^2\psi]^{\frac{1}{2}} d\psi;$$

$\Delta\sigma$ is the stress range,
a is the crack depth,
2c is the crack length,
$\sigma_{yield}$ is the yield stress,
$\sigma_{max}$ is the maximum applied stress,
$\psi$ is the angle in the crack plane with respect to the crack length.

For a given applied stress, the stress intensity range $\Delta K_i$ may thus be calculated from a knowledge of the metallurgy of the part (i.e., $\sigma_{yield}$), the crack depth a, and the depth to length ratio.

Assuming the crack is in the Paris regime of validity, the crack depth increase per unit fatigue cycle da/dN is $$da/dN = A(\Delta K_i)^m \tag{2}$$

where a and m are material constants. The remaining life for a number of cycles to failure $\Delta N$ is then $$\Delta N = \frac{2}{(m-2)A(CQ^{-\frac{1}{2}}\Delta\sigma)^m} \tag{3}$$

$$\left[\frac{1}{a^{(m-2)/2}} - \frac{CQ^{-\frac{1}{2}}\sigma_{max}}{K_{IC}}\right]^{m-2}$$

Failure is imminent, i.e., N=0, when $$a_c = \left(\frac{K_{IC}}{CQ^{-\frac{1}{2}}\sigma_{max}}\right)^2 \tag{4}$$

Equation 4 may be used to estimate the critical flaw sizes of typical structural materials. Thus, as can be seen from the above analysis, aside from the metallurgical properties of a material, the most important fracture mechanics parameters which nondestructive evaluation must supply are the depth and length of a flaw. Further analysis may be used to relate ultrasonic measurements to the quantities of flaw depth and length.

Utilizing geometrical and optical diffraction theory, when a flaw is long and deep compared to the Rayleigh wavelength in the material, a model may be formulated to facilitate analysis of both the angular and frequency dependencies of the Rayleigh wave scattering by a surface flaw. The interaction may be viewed as being concentrated near the surface, since the fields of the wave propagating on a free surface diminish rapidly as they reach deeper into the material and thus are essentially unable to probe the region near the crack tip. In this context, the back scattered radiation pattern represents the Fourier transform of the complex amplitude distribution across an irradiated aperture. Thus in general, using the mathematical expression of the Huygenes/Fresnel principle, the field amplitude at a point ($u_o$, $v_o$) can be written as $$U(u,v) = \iint_{-\infty}^{\infty} h(u,v;x,y) U(x,y) dxdy \tag{5}$$

where:

$$h(u,v;x,y) = (1/i\lambda) \frac{1}{r} \exp(ikr) \cos(\bar{n},\bar{r})$$

and u(x,y) is the complex amplitude distribution across the aperture and is identically zero outside the aperture. k is the wave number and r is the distance between points (x,y) and (u,v). $\cos(\bar{n},\bar{r})$ is the obliquity factor and is approximately equal to one in this case, where the distance to the detector is much greater than the maximum linear dimensions of the aperture and where only a finite region about the aperture normal is used. The distance r is given by $r^2 = R^2 + (u-x)^2 + (v-y)^2$. If the Fraunhounfer approximation $R \gg \frac{1}{2} k(x^2+y^2)$ is adopted, the quadratic phase factor in the amplitude expression is approximately unity over the entire aperture and the observed field distribution can thus be found directly from a Fourier transform of the aperture distribution itself. Thus, $$U(u,v) = C \iint_{-\infty}^{\infty} U(x,y) \exp[-(ik/R)(ux+vy)]dxdy \tag{6}$$

where $C = (1/i\lambda R) \exp[(ik/2R)(x^2+y^2)]$.

For a rectangular aperture with sides $l_x$ and $l_y$ normally illuminated by a unit amplitude, monochromatic wave $$U(u,v) = C l_x l_y \operatorname{Sinc}(l_x f_x) \operatorname{Sinc}(l_y f_y) \tag{7}$$

where $f_x = u/\lambda R$ anf $f_y = v/\lambda R$ are the frequencies at which the Fourier transform is evaluated. The intensity (the square of the absolute value of u) is thus $$I(u,v,) = \frac{l_x^2 l_y^2}{\lambda^2 R^2} \operatorname{Sinc}^2 \frac{l_x u}{\lambda R} \operatorname{Sinc}^2 \frac{l_y v}{\lambda R}. \tag{8}$$

In the present context, in which the interaction between surface ultrasonic waves and a crack is examined, the result is specialized to a very narrow aperture of length 2c, so that the intensity is approximately given by $$I(\alpha,\theta,\omega) = I(O,O,\omega)(\sin^2\psi)/\psi^2 \tag{9}$$

where $\psi = (c\omega/V_R)(\sin\alpha + \sin\theta)$. $\psi$ takes into account the oblique incidence of the radiation from the transmitter with an angle $\alpha$ to the aperture normal. In a backscattering experiment (such as typically encountered in a commercial application) $\alpha = \theta$ where $\theta$ is the angle of the receiver with respect to the crack normal. $V_r$ is the Rayleigh wave velocity, $\omega$ is the frequency in radians and I(O,O,$\omega$) is the intensity at $\alpha=0$, $\theta=0$ at a given frequency. The crack radius c may then be obtained from calculations based upon the observed positions of nulls (or peaks) in the angular ($\alpha,\theta$) or frequency ($\omega$) distribution of the radiation pattern. The fields U(x,y) and V(u,v) in Equation 6 are related by a two-dimensional Fourier transform. The inverse transform may be used to give the source distribution U(x,y) from the measured or otherwise known remote field distribution, $$U(x,y) = C \iint_{-\infty}^{\infty} U(u,v) \exp[-(ik/R)(ux+vy)] dxdy \tag{10}$$

Carrying out a procedure to evaluate Equation 10 from known or measured field distributions constitutes the inverse scattering problem. The specific evaluation of Equation 10 is dependent on the nature of the field distribution and the data format.

At this point, the specific measurement goals of this analysis come into play and the inversion problem is limited to obtaining the desired fracture mechanics parameters, i.e., crack length and depth. The Fraunhofer radiation pattern described in Equation 9 is ideally suited to accomplishing a length calculation by virtue of the nulls and the peaks of the sinc function in that distribution. The crack radius may be obtained by calculations based on the observed positions of the nulls or peaks in the angular $(\alpha, \theta)$ or frequency $(\omega)$ dependence of the radiation pattern, i.e., from the position of the nth null from broadside $$c = \frac{nV_R}{\omega} / (\sin\alpha + \sin\theta). \tag{11}$$

Since each of the nulls or peaks, by virtue of its position, can be used to predict the length of a crack with the aid of the model; a statistical distribution of estimates may be obtained from a set of nulls and peaks. Comparisions between crack radii estimates and actual values obtained by micrographical examination have in experiments shown agreement by this method within about 10%. The crack lengths estimated from the data are at most equal to real crack lengths because of the shape of the crack under the surface, which provides a diminishing effective crack length with depth. For semi-circular cracks, this treatment is sufficient to provide a good estimate of crack dimensions. Whenever elliptically shaped cracks are encountered, however, the crack depth, or the crack depth to length ratio, must also be obtained for use in fracture mechanics life predictions.

It is an outstanding feature of this invention to provide a method for measuring the depth of a flaw in a material by utilizing acoustic surface waves. Now referring to FIG. 1, illustrated in a partially schematic perspective view is an apparatus for practicing the method of the present invention. In FIG. 1, an object 10 to be evaluated has developed a part through surface crack 12, which is illustrated, for clarity, in somewhat exaggerated dimensions. A transmitting transducer 14 is positioned on the object so as to generate an acoustic surface wave, as represented by the line 16, travelling toward the crack 12. A signal generator 18 is provided to drive the transducer 14 at the appropriate frequency. A receiving transducer 20 is positioned on the object 10 so as to receive surface acoustic waves reflected from the crack 12 at a particular angle $\alpha$, as illustrated by the line 22. The output of the transducer 20 is boosted in an amplifier 24 and from there is routed to a digitizer 26 to convert the signal to a digital signal, which is then applied to a computer 28, which performs a Fourier transform on the signal, converting it from the time domain to the frequency domain, the purpose of which will be further explained below. The output of the amplifier 24 may also be applied to a recorder 30 to provide a record of the signal output from the receiving transducer 20.

In order to perform the method of this invention, the crack 12 is irradiated with an incident acoustic surface wave signal from the transmitting transducer 14. The receiving transducer 20 then is used to detect a reflected acoustic surface wave signal, which will include a first portion, indicated by the solid portion of line 22, reflected from the surface edge of the flaw, and a second portion, indicated by the dotted portion of line 22, which will be reflected from the bottom of the crack. The depth of the crack is then determined by analyzing the interference between the first and second portions of the reflected signal, utilizing the peaks or nulls appearing in the reflected signal. In one embodiment, the transmitting transducer 14 is utilized to irradiate the flaw with a short pulse incident wave, which will contain a broadband of frequencies. The computer 28 is then used to Fourier transform the reflected signal from the time domain to the frequency domain. Furthermore, a reflected signal is detected at at least two different angles $\alpha$ with respect to the normal to the flaw direction. The frequency domain signals are then examined and a frequency $f_n$ is selected at which a well defined maximum or a well defined minimum amplitude was detected independent of the angle of detection. The depth a of the crack can then be determined from the formula $$a = (N\ V_r/2f_n). \tag{12}$$

The minimums in the interference pattern should preferably be used, but in cases where excessive noise in the data obscures the minima, the maxima may be employed to calculate the depth of the crack.

Figure 2:
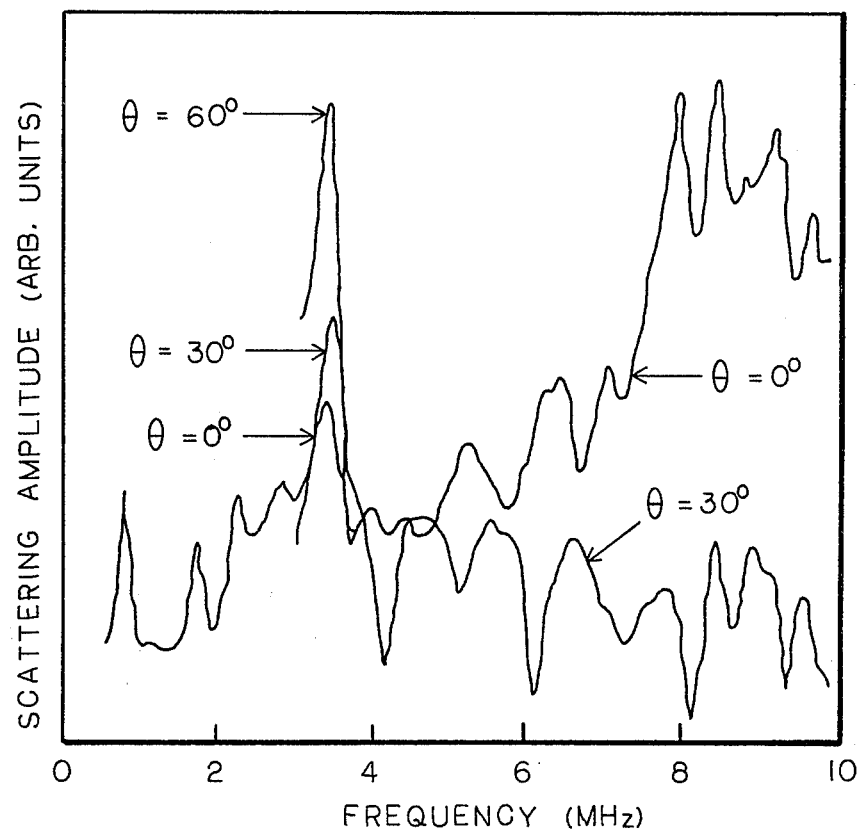
FIG. 2 is a plot illustrating the frequency dependence of the scattering amplitude obtained at various angles of reflection utilizing the method of this invention.

Now referring to FIG. 2, some typical frequency domain plots obtained utilizing this embodiment of the method are illustrated. FIG. 2 shows a plot of the scattered amplitude as a function of frequency for a slot of length 0.254 centimeters and depth 0.039 millimeters, which was spark erosion cut into a plate of commercial aluminum. The principal feature of the graph is a peak at 3.45 MHz which remains stationary in frequency as the receiver angle is changed, in contrast to the other peaks which form a background that changes rapidly with angle. The peak arises because of interference between the waves scattered from the crack tip and those scattered by the edge where the slot breaks the surface of the plate. The accuracy of the crack depth which was estimated by this invention is given in Table I for two different crack depths.

TABLE I

| | | CRACK DEPTH ESTIMATION | | | |
|---|---|---|---|---|---|
| Detected Angle $\theta$ (deg) | Peak Freq. (MHz) | Est. Depth (mm) | Mean Est. Depth (mm) | "True" Depth (mm) | Percent Error (%) |
| 0 | 3.45 | .412 | | | |
| 30 | 3.47 | .409 | | | |
| 60 | 3.40 | .418 | | | |
| 90 | 3.40 | .418 | | | |
| 120 | 3.42 | .415 | | | |
| 150 | 3.50 | .406 | 0.408 | 0.38 | 3% |
| 180 | 3.45 | .412 | | | |
| 210 | 3.50 | .406 | | | |
| 240 | 3.90 | .364 | | | |
| 270 | 3.40 | .418 | | | |
| 0 | 1.34 | .107 | | | |
| 20 | 1.34 | .107 | | | |
| 30 | 1.33 | .106 | | | |
| 45 | 1.32 | .099 | 0.104 | 0.102 | 2% |
| 60 | 1.60 | .089 | | | |
| 75 | 1.35 | .105 | | | |
| 90 | 1.22 | .116 | | | |

Figure 3:
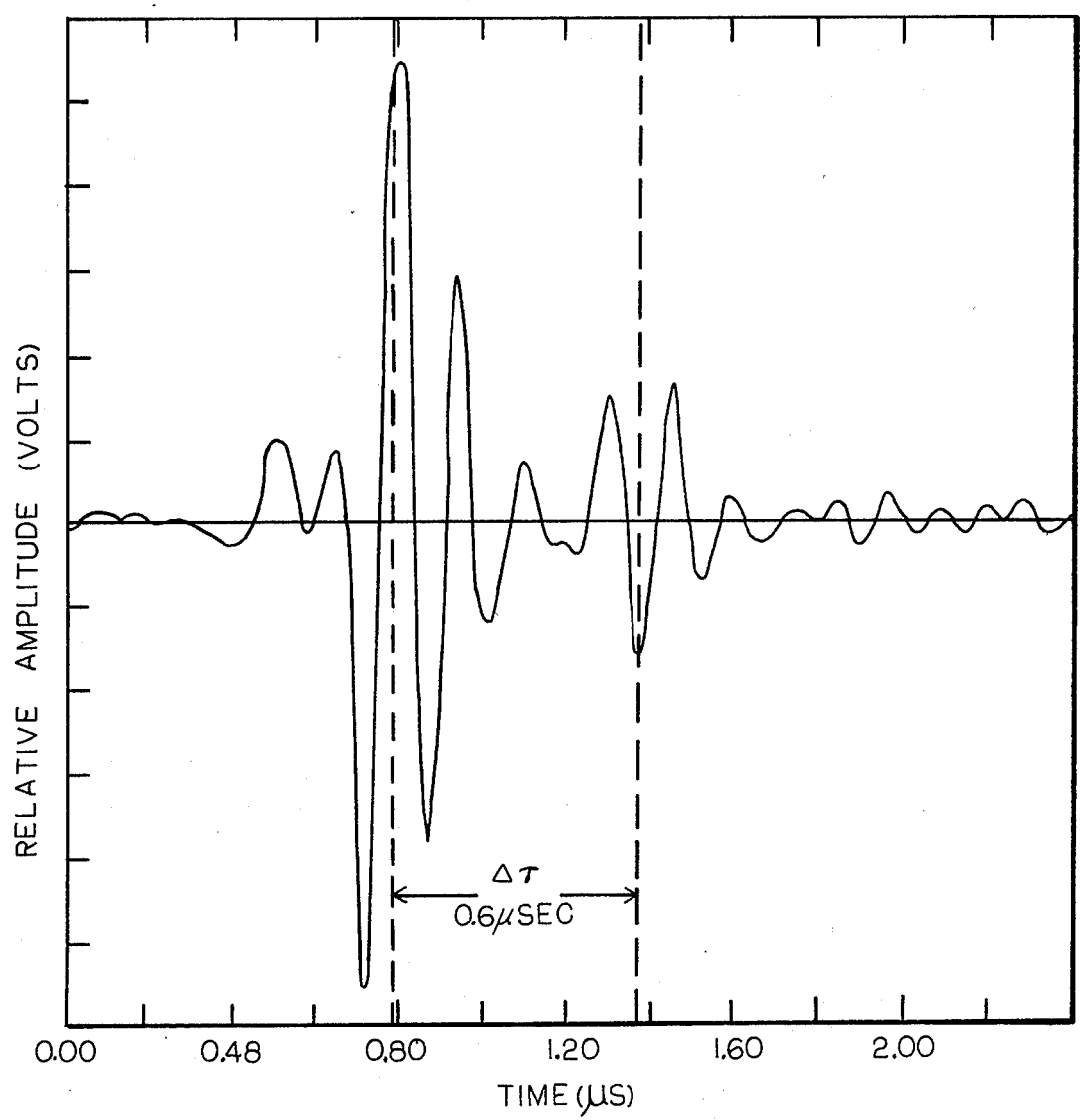
FIG. 3 is a plot of amplitude versus time illustrating the time domain signal obtained from a fatigue crack using the method of the present invention.
Figure 4:
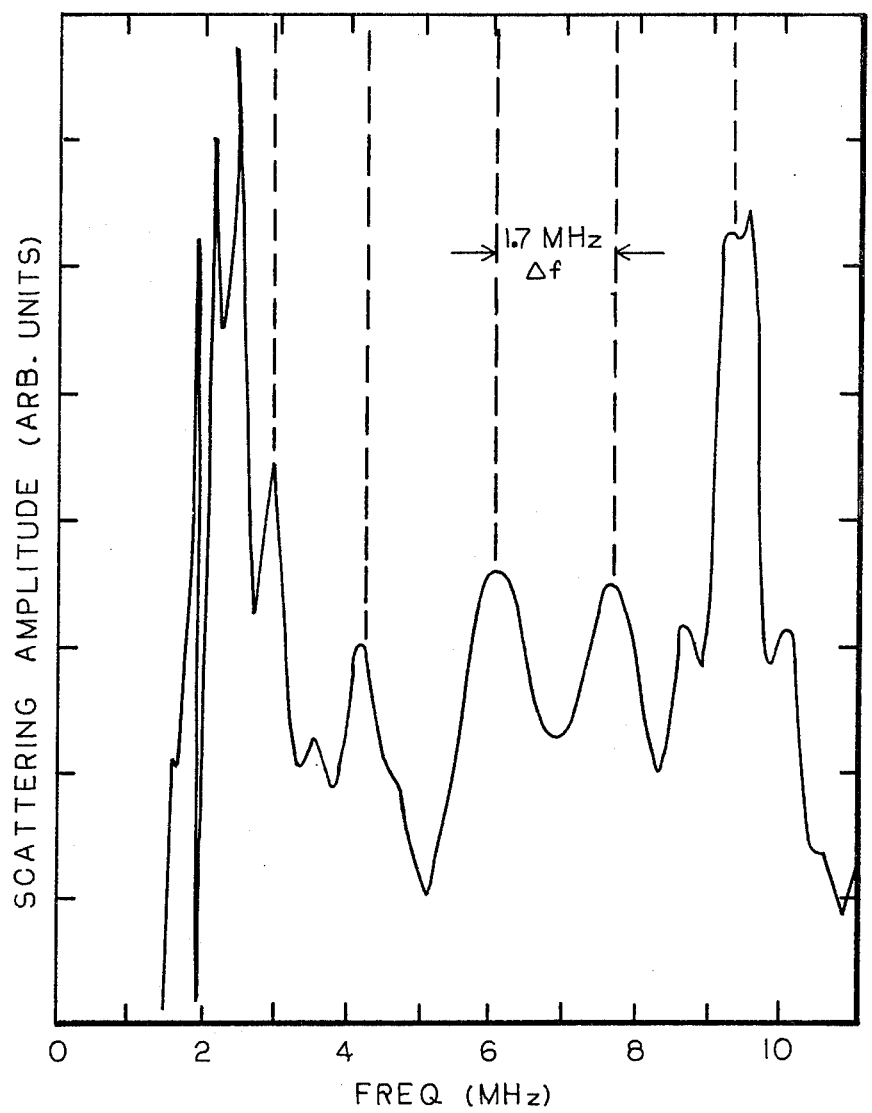
FIG. 4 is a plot of amplitude versus frequency illustrating the frequency domain signal obtained in applying the method of the present invention to the measurement of crack depth.

Another embodiment of the method of this invention may be explained by first referring to the time domain of the received signal. For sufficiently short pulses, the different signals from the extremities of the crack can be resolved such that an analysis in the time domain is possible. This procedure is exemplified in FIG. 3, which shows an RF waveform for a pulse echo experiment. The spacing between the two waveforms shown in the figure corresponds to a path length equal to twice the depth of the crack. The second signal is thought to come primarily from the crack bottom because the curved sides of the crack are more likely to deflect the waves out of the beam of interest by multiple reflections inside the crack in accordance with Snell's law. The shape of the waveforms in the time domain, however, and the close spacing of the signals, frequently makes it difficult to pinpoint the exact point in time from which to measure the interval. Thus, it is frequently convenient to convert the time domain signal to a frequency domain signal. The existence of two somewhat separated pulses in the time domain is equivalent to interference in the frequency domain. FIG. 4 shows the magnitude of the Fourier transform of the time domain signal of FIG. 3. With frequency data such as that shown in FIG. 4, the depth a of the crack can be computed by the method of this invention from the formula $a = nV_r/2f_n$ where n is an integer, $V_r$ is the speed of an acoustic surface wave in the object, and $f_n$ is the nth minimum or maximum in the frequency domain of the reflected signal. In practicing this embodiment of the invention, it is preferable to irradiate the flaw from a direction normal to the flaw direction and to detect the reflected acoustic surface wave signal at a direction normal to the flaw direction. In the latter instance, it is not necessary to use a separate receiving transducer 20, as shown in FIG. 1, and the transmitting transducer 14 may also be used to receive the reflected signals, an arrangement utilizing the pulse-echo technique.

Another embodiment of the method may be utilized where a narrowband source of acoustic surface waves is utilized. In this embodiment, the crack is irradiated with a series of incident acoustic surface wave signals, each at a different frequency. A reflected acoustic surface wave signal is then detected for each incident signal at at least two different angles with respect to the normal to the flaw direction and the frequency $f_n$ for which a maximum or minimum amplitude is detected, independent of the angle of detection, is substituted into the above depth formula to compute the crack depth.

From measured crack depth and length, one can readily proceed, by the analysis discussed above, to a prediction of remaining life for a part. From published crack growth data for Ti-6-4, for example, the crack growth rate is $da/dN = 3.4 \times 10^{-11}(\Delta K)^{3.9}$. Under the assumption that $K_{IC} = 55$ ksi $\sqrt{\text{in}}$, $\sigma_{max} = 0.5\sigma_{yield} = 70$ ksi; and further assuming that $\Delta\sigma = \sigma_{max} = 70$ ksi, one can obtain from a sample crack depth of a $=0.9$ mm and a length 2c of 2.85 mm a value for the reduced stress intensity factor $k_I = 0.240$ (inches)$^{\frac{1}{2}}$ and $\Delta N = 14,900$ cycles to failure. An indication of the influence of error on depth estimation is afforded by carrying out the calculation for a slightly greater depth leaving all other parameters invariant. For a $=1.1$ mm, $\Delta N = 13,300$ cycles, or a difference of about 10% in remaining life, for an uncertainty of 20% in the depth a.

It has been observed experimentally that the speed of Rayleigh waves $V_R$ in a crack is slightly less than would be expected, presumably due to a waveguiding effect. Thus, it may be desirable to compensate $V_R$ for this effect in performing depth calculations according to this invention.

In conclusion, although typical embodiments of the present invention have been illustrated and discussed above, numerous modifications and alternative embodiments of the method of this invention will be apparent to those skilled in the art in view of this description. Accordingly, this description is to be considered as illustrative only and is provided for the purpose of teaching those skilled in the art the manner of performing the method of this invention. Furthermore, it should be understood that the forms of the invention depicted and described herein are to be considered as the presently preferred embodiments. Various changes may be made in the configurations, size, and arrangements of the components, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit attained through reading the above description of the invention.

What is claimed is:

1. A method for measuring the depth a of a surface breaking flaw in an object, comprising the steps of:
   (a) irradiating the flaw with an incident acoustic surface wave signal;
   (b) detecting a reflected acoustic surface wave signal, including a first portion reflected from the surface edge of the flaw and a second portion reflected from the bottom of the flaw; and
   (c) determining the depth of the flaw by analyzing the interference between the first and second portions of the reflected signal.

2. The method of claim 1, wherein step (a) further comprises:
   (a) irradiating the flaw with a short pulse incident acoustic surface wave signal containing a broadband of frequencies.

3. The method of claim 2, wherein step (c) further comprises:
   (c) transforming the reflected signal from the time domain to the frequency domain and computing the depth a of the flaw from the formula $a = nV_r/2f_n$, where n is an integer, $V_r$ is the speed of an acoustic surface wave in the object, and $f_n$ is the nth minimum or maximum in the frequency domain of the reflected signal.

4. The method of claim 3, wherein step (a) further comprises irradiating the flaw from a direction normal to the flaw direction.

5. The method of claim 4, wherein step (b) further comprises detecting a reflected acoustic surface wave signal at a direction normal to the flaw direction.

6. The method of claim 2, wherein step (b) further comprises:
   (b) detecting a reflected acoustic surface wave signal at at least two different angles with respect to the normal to the flaw direction; and step (c) further comprises
   (c) transforming the reflected signals from the time domain to the frequency domain, selecting a frequency $f_n$ for which a maximum or minimum amplitude is detected independent of the angle of detection, and calculating the depth a from the formula $a = nV_r/2f_n$, where n is an integer, and $V_r$ is the speed of an acoustic surface wave in the object.

7. The method of claim 1, wherein step (a) further comprises:
   (a) irradiating the flaw with a series of incident acoustic surface wave signals, each at a different frequency.

8. The method of claim 7, wherein step (b) further comprises:
   (b) detecting, for each incident signal, a reflected signal at at least two different angles with respect to the normal to the flaw direction; and step (c) further comprises
   (c) selecting the frequency $f_n$ for which a maximum or minimum amplitude is detected independent of the angle of detection and calculating the depth a from the formula $a = nV_r/2f_n$, where n is an integer, and $V_r$ is the speed of an acoustic surface wave in the object.

9. The method of claim 8, wherein step (a) further comprises irradiating the flaw from a direction normal to the flaw direction.

10. A method for measuring the depth a of a surface breaking flaw in an object, comprising the steps of:
   (a) irradiating the flaw from a direction normal to the flaw direction with a short pulse incident acoustic surface wave signal containing a broad band of frequencies;
   (b) detecting a reflected acoustic surface wave signal at a direction normal to the flaw direction, including a first portion reflected from the surface edge of the flaw and a second portion reflected from the bottom of the flaw; and
   (c) transforming the reflected signal from the time domain to the frequency domain; and
   (d) computing the depth a of the flaw from the formula $a = nV_r/2f_n$, where n is an integer, $V_r$ is the speed of an acoustic surface wave in the object, and $f_n$ is the nth minimum or maximum in the frequency domain of the reflected signal.

11. A method for measuring the depth a of a surface breaking flaw in an object, comprising the steps of:
   (a) irradiating the flaw from a direction normal to the flaw direction with a short pulse incident acoustic surface wave signal containing a broad band of frequencies;
   (b) detecting a reflected acoustic surface wave signal, including a first portion reflected from the surface edge of the flaw and a second portion reflected from the bottom of the flaw, at at least two different angles with respect to the normal to the flaw direction;
   (c) transforming the reflected signal from the time domain to the frequency domain; and
   (d) selecting a frequency $f_n$ for which a maximum or minimum amplitude is detected independent of the angle of detection; and
   (e) calculating the depth a of the flaw from the formula $a = nV_r/2f_n$, where n is an integer, and $V_r$ is the speed of an acoustic surface wave in the object.

12. A method for measuring the depth a of a surface breaking flaw in an object, comprising the steps of:
   (a) irradiating the flaw from a direction normal to the flaw direction with a series of incident acoustic surface wave signals, each at a different frequency;
   (b) detecting, for each incident signal, a reflected acoustic surface wave signal at at least two different angles with respect to the normal to the flaw direction;
   (c) selecting the frequency $f_n$ for which a maximum or minimum amplitude is detected independent of the angle of detection; and
   (d) calculating the depth a from the formula $a = nV_r/2f_n$, where n is an integer, and $V_r$ is the speed of an acoustic surface wave in the object.

* * * * *